United States Patent [19]

Eberle et al.

[11] 3,992,396

[45] Nov. 16, 1976

[54] 2-AMINO-5-(SUBSTITUTED OR UNSUBSTITUTED PHENYLALKYL)-THIADIAZOLES

[75] Inventors: Marcel K. Eberle, Madison; Robert E. Manning, Mountain Lakes, both of N.J.

[73] Assignee: Sandoz, Inc., E. Hanover, N.J.

[22] Filed: Nov. 29, 1974

[21] Appl. No.: 528,476

Related U.S. Application Data

[63] Continuation-in-part of Ser. No. 485,991, July 5, 1974, abandoned, which is a continuation-in-part of Ser. No. 452,678, March 20, 1974, abandoned, which is a continuation-in-part of Ser. No. 218,559, Jan. 17, 1972, abandoned, which is a continuation-in-part of Ser. No. 124,489, March 15, 1971, abandoned.

[52] U.S. Cl. .................. 260/306.8 D; 260/552 SC; 424/270
[51] Int. Cl.² ..................................... C07D 285/12
[58] Field of Search ........................... 260/306.8 D

[56] References Cited

UNITED STATES PATENTS 2,524,729   10/1950   Kyrides et al. ............... 260/306.8 D

OTHER PUBLICATIONS

Elderfield, (ed.), *Heterocyclic Compounds*, vol. 7, Wiley, N.Y., 1961, pp. 587–595.

*Primary Examiner*—R. J. Gallagher
*Attorney, Agent, or Firm*—Gerald D. Sharkin; Robert S. Honor; Thomas O. McGovern

[57] ABSTRACT

2-amino-5-(substituted or unsubstituted phenylalkyl)-thiadiazoles, e.g., 2-amino-5-(4-[phenylbutyl])-thiadiazole, prepared, e.g., by ring closure, of corresponding 1-(substituted or unsubstituted phenylalkanoyl)-thiosemicarbazide in a strong acid medium. The compounds are useful as minor tranquilizers and sedative hypnotics.

18 Claims, No Drawings

2-AMINO-5-(SUBSTITUTED OR UNSUBSTITUTED PHENYLALKYL)-THIADIAZOLES

This application is a continuation-in-part of application Ser. No. 485,991, filed July 5, 1974, which in turn is a continuation-in-part of application Ser. No. 452,678, filed Mar. 20, 1974, which in turn is a continuation-in-part of application Ser. No. 218,559, filed Jan. 17, 1972, which in turn is a continuation-in-part of application Ser. No. 124,489, filed Mar. 15, 1971, all now abandoned.

This invention relates to 2,5-substituted thiadiazoles. More particularly, it relates to 2-amino-5-(substituted or unsubstituted phenylalkyl)-thiadiazoles, intermediates thereof to processes for their preparation, and pharmaceutically acceptable acid addition salts.

The compounds of this invention may be represented by the following structural formula:

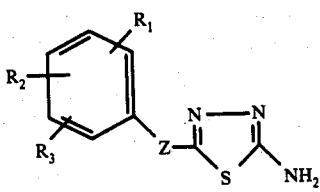

(I)

where
R$_1$, R$_2$, and R$_3$ are independently hydrogen, lower alkyl having 1 to 4 carbon atoms, e.g., methyl, ethyl, propyl, isopropyl, butyl, or isobutyl, lower alkoxy having 1 to 4 carbon atoms, e.g., methoxy, ethoxy, propoxy, isopropoxy, butoxy or isobutoxy, or halo having an atomic weight of 19 to 36, and Z is

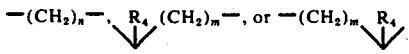

where
R$_4$ is lower alkyl having 1 to 4 carbon atoms, as stated above,
n is 1, 2, 3, 4, 5, 6, 7 or 8, and
m is 0, 1, 2, 3, 4, 5, 6 or 7
provided that when R$_1$, R$_2$, and R$_3$ are hydrogen, or one of R$_1$, R$_2$, and R$_3$ is methyl and Z is —(CH$_2$)$_n$—, then n is other than 1 or 2, and that when more than one of R$_1$, R$_2$, and R$_3$ is t-butyl, they are bonded to other than adjacent carbon atoms.

The compounds of formula (I) may also be represented by the following structural formulae:

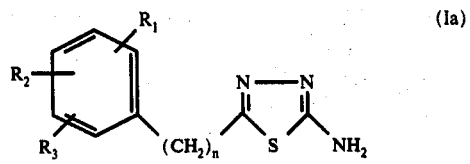

(Ia)

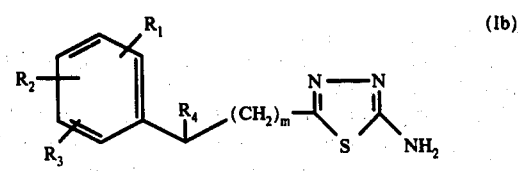

(Ib)

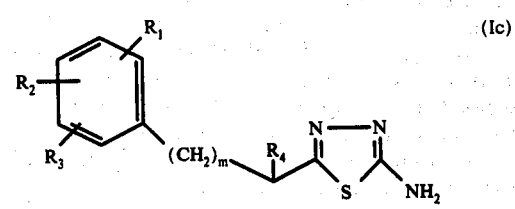

(Ic)

wherein R$_1$, R$_2$, R$_3$, R$_4$, m, n and the proviso have the above stated significance.

The compounds of formula (I) may be prepared by the following reaction scheme A:

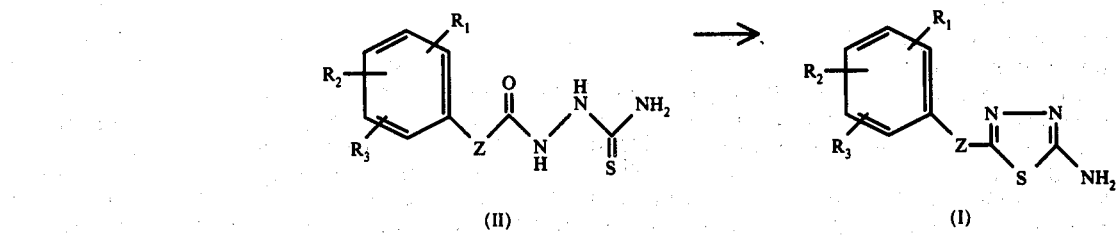

wherein R$_1$, R$_2$, R$_3$, Z and the proviso have the above stated significance.

The compound of formula (I) may be prepared by ring closure of a compound of formula (II) in a strong Lewis acid medium such as phosphoric acid, hydrochloric acid, sulfuric acid, and the like, or a halogenated phosphoric acid, such as phosphorous tribromide, at a temperature of from 40° to 100° C., preferably 50° to 65° C., for about 0.5 to 20 hours, preferably 2 to 6 hours. Though a solvent is not necessary, inert aromatic solvents such as benzene, toluene, xylene, chlorobenzene and the like may be used. Neither the temperatures nor the times used are critical.

The compounds of formula (I) may also be prepared by the following reaction scheme B:

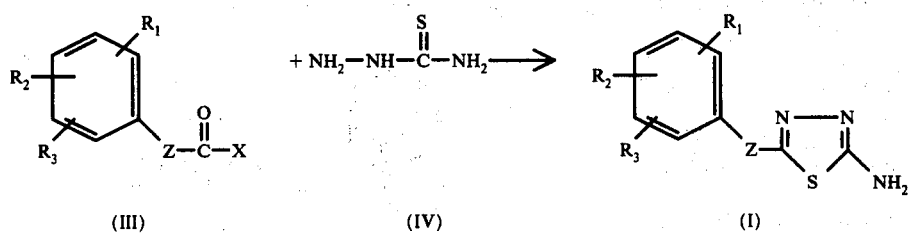

wherein $R_1$, $R_2$, $R_3$, Z and the proviso have the above stated significance, and X is halo having an atomic weight of 35 to 80.

The compounds of formula (I) may be prepared by treating a substituted or unsubstituted phenylalkanoyl-halide, e.g., 5-phenylvaleroyl chloride, with thiosemicarbazide in a strong Lewis acid medium such as described respecting scheme A at a temperature of from 40° to 100° C., preferably 50° to 65° C., for about 0.5 to 20 hours, preferably about 2 to 6 hours. Though a solvent is not necessary, inert solvents such as described respecting scheme A may be used if desired. Neither the temperatures nor the times used are critcal.

The compounds of formula (II) may be prepared by the following reaction scheme C:

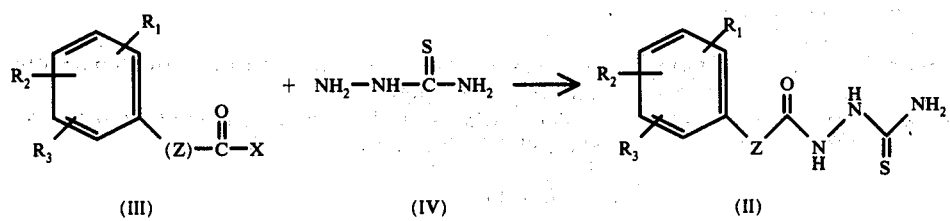

wherein $R_1$, $R_2$, $R_3$, Z, X and the proviso have the above stated significance.

The compounds of formula (II) may be prepared by treating a compound of formula (III) with thiosemicarbazide in an inert solvent such as dialkylformamide, e.g., dimethylformamide, at a temperature of from 0° to 80° C., preferably 15° to 50° C., for about 1 to 24 hours, preferably 2 to 6 hours. Neither the solvents nor the temperature or time used is critical.

The compounds of formula (II) may also be prepared by the following reaction scheme D:

wherein $R_5$ is lower alkyl as defined above, and $R_1$, $R_2$, $R_3$, Z and X have the above stated significance.

The compounds of formula (II) may be prepared in the first step by treating a compound of formula (III) with an excess of hydrazine (VI) in an inert solvent such as the ethers, e.g., methylether, ethylether, diethylether and the like, or the aromatic hydrocarbons such as benzene, toluene and the like, optionally in the presence of an alkali metal carbonate, e.g., potassium carbonate, sodium carbonate and the like, preferably sodium carbonate, at a temperature of from 20° C. to the reflux temperature of the solvent, preferably at room temperature for about 1 to 8 hours, preferably 3 to 5 hours, to give the intermediate compound (VII). In the second step, compound (VII) is dissolved in concentrated hydrochloric acid or concentrated sulfuric acid and treated with an excess of potassium thioisocyanate or sodium thioisocyanate (VIII) at the reflux temperature of the aqueous acid medium for about 1 to 8 hours, preferably 3 to 5 hours. Neither the temperature nor the time used is critical.

The compounds of formula (II) may alternatively be prepared by treating a compound of formula (V) in the first step with an excess of hydrazine (VI) in an aqueous or inert solvent such as the lower alkanols having 1 to 4 carbon atoms, e.g., methanol, ethanol, and the like, or the aromatic hydrocarbons such as benzene, toluene and the like, at a temperature of from 0° to

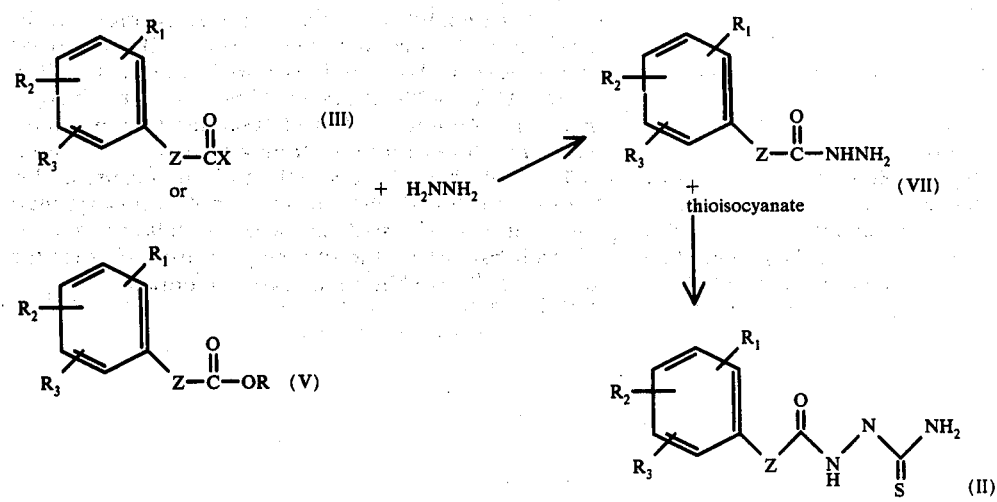

120° C., preferably at reflux temperature of the solvent, for 1 to 4 hours, preferably 1 to 2 hours, to give the intermediate compound (VII). Compound (VII) is then treated as described in step two above. Neither the temperature nor the time used is critical.

The compounds of formulae (I) and (II) may be recovered by conventional recovery techniques such as crystallization.

Certain of the compounds of formulae (III), (IV), (V), and (VII) are known and may be prepared by methods disclosed in the literature. Those compounds of formulae (III), (IV), (V), and (VII) not specifically disclosed may be prepared according to analogous methods from known materials.

The compounds of formula (I) are useful because they possess pharmacological activity. In particular, the compounds are useful as central nervous system depressants, especially as sedative-hypnotics and minor tranquilizers as indicated by (1) their ability to produce docility in behavior tests in mice given 25 to 200 mg/kg of animal body weight, i.p. of the test compound according to the 30-word adjective check sheet system basically as described by Irwin S. Gordon (Research Conference, Medicinal Chemistry, 1959) and Chen (Symposium on Sedative and Hypnotic Drugs, Williams and Wilkins, 1954); (2) by their ability to antagonize chronic convulsions and death in mice given 50 to 250 mg/kg i.p. of N-sulfamoylazepine; (3) by the hexobarbital reinduction method of Winter, (J. Pharmacol and Exp. Therap., 94, 7–11, 1948) in which the reinduction of anesthesia after recovery from hexobarbital induced anesthesia is used to determine sedative-hypnotic activity in mice given 70 mg/kg of animal body weight, i.p. of hexobarbital followed immediately after the mice regain their righting reflexes by 25 to 200 mg/kg of animal body weight, i.p. of the test compound; (4) as indicated in Cebus monkey using chlonically implanted electrodes. Brain readings are obtained via a ten or sixteen channel electroencephalograph. For the recording sessions, the monkeys are restrained by neck and waist plates in chairs in full side observation cages at the same time every night for thirteen and one half hours Monday through Thursday. Gross behavior is monitored via closed circuit television and video tape recordings. The compounds of formula (I) are administered p.o. at a dosage of from about 1.8 to about 30 mg/kg immediately on placing the monkey in the observation cages with at least seven days intervening between drug administration. Physiological saline is administered via a similar route and at the same times on all control runs. Control data are collected at least three days per week and accumulated to give control data for fifteen sessions per monkey. Data from each session are statistically compared via computer analysis to the previous 5–15 control sessions for the particular animal, with particular emphasis given to the following phases of the sleep-wakefulness cycle: resting awake, light sleep, deep sleep, paradoxical (REM) sleep, "pseudo-"paradoxical sleep, latency to onset of deep sleep, and latency to onset of first epoch of paradoxical sleep; and (5) as indicated in the cat given typically 5 to 30 mg/kg of animals body weight of the active material and tested in sleep studies using chronic cortical and subcortical electrode placements, with eye movement measured via electro-oculogram. Brain readings are obtained via Gross Model 6 electroencephalograph, and the gross behavior of the animal is monitored via closed circuit television and video tape recordings.

For such usage, the compounds may be administered orally or parenterally as such or admixed with conventional pharmaceutical carriers.

The dosage of active ingredient employed for minor tranquilizer use may vary depending on the severity of the condition being treated. However, in general, satisfactory results are obtained when a compound of formula (I) is administered at a daily dosage of from about 1 milligram to about 150 milligrams per kilogram of animal body weight p.o., preferably given in divided doses 2 to 4 times a day, or in sustained release form. For most larger mammals (e.g., primates), the total daily dosage is from about 75 milligrams to about 1500 milligrams. Dosage forms suitable for internal use comprise from about 18 to about 750 milligrams of active compound in intimate admixture with a solid or liquid pharmaceutically acceptable carrier or diluent.

The dosage of active ingredient employed for sedative-hypnotic use may vary depending on the severity of the condition being treated. However, in general, satisfactory results are obtained when a compound of the formula (I) is administered at a daily dosage of from about 1 milligram to about 150 milligrams per kilogram of animal body weight p.o., typically given in a single dose at bedtime. For most larger mammals, the total daily dosage is from about 75 milligrams to about 1500 milligrams, preferably at bedtime in a single dose.

Furthermore, the compounds of formula (I) may be similarly administered in the form of their non-toxic, pharmaceutically acceptable acid addition salts. Such salts possess the same order of activity as the free base and are readily prepared by reacting the base with an appropriate acid and, accordingly, are included within the scope of the invention. Representative of the acid addition salts are the mineral acid salts, such as the hydrochloride, hydrobromide, sulfate, phosphate and the like, and the organic acid salts, such as succinate, benzoate, acetate, p-toluenesulfonate, benzenesulfonate and the like.

EXAMPLE 1

2-amino-5-(4-[phenylbutyl])-thiadiazole

Step A: 1-(5-phenylvaleroyl)-3-thiosemicarbazide.

A mixture of 9.9 g. of 5-phenylvaleroylchloride and 4.6 g. of thiosemicarbazide was stirred in 20 ml. of dimethylformamide for 6 hours at 22° C. The solvent was evaporated and 10 ml. of water and 10 ml. of ether were added to the residue. The precipitate was filtered off to give the intermediate 1-(5-phenylvaleroyl)-3-thiosemicarbazide, m.p. 140°–141° C.

Step B: 2-amino-5-(4-[phenylbutyl])-thiadiazole.

A mixture of 5.0 g. of 1-(5-phenylvaleroyl)-3-thiosemicarbazide (from Step A) and 5.4 g. of phosphorous tribromide was heated to 60°–65° C. for 2 hours After cooling, 50 cc. of cold water and then 3 cc. of a 50% sodium hydroxide solution were added. The product, 2-amino-5-(4-[phenylbutyl])-thiadizole, m.p 172°–174° C. was precipitated.

EXAMPLE 2

Step A

Following the procedure of Example 1, Step A, and in place of 5-phenylvaleroylchloride and starting with 1. 4-phenylbutanoylchloride, 2. 6-phenylhexanoylchloride,
3. 2-(p-chlorophenyl)acetylchloride,
4. 2-(6-chlorophenyl)acetylchloride,
5. 5-(p-methoxyphenyl)pentanoylchloride,
6. 2-(5-chlorophenyl)acetylchloride,
7. 2-(2,6-dichlorophenyl)acetylchloride,
8. 2-(3,4-dichlorophenyl)acetylchloride,
9. 2-(2,4-dichlorophenyl)acetylchloride,
10. 2-(2-fluorophenyl)acetylchloride,
11. 2-(3-fluorophenyl)acetylchloride,
12. 2-(4-fluorophenyl)acetylchloride,
13. 2-(2,3,6-trichlorophenyl)acetylchloride,
14. 5-(p-chlorophenyl)pentanoylchloride,
15. 7-(phenylhepanoylchloride,
16. 8-phenyloctanoylchloride, or
17. 9-phenylnonanoylchloride, the following intermediates are obtained:

1. 1-(4-phenylbutanoyl)-3-thiosemicarbazide, m.p. 213°–214° C.,
2. 1-(6-phenylhexanoyl)-3-thiosemicarbazide, m.p. 119°–121° C.,
3. 1-(2-[p-chlorophenyl]acetyl)-3-thiosemicarbazide, m.p. 178°–180° C.,
4. 1-(2-[6-chlorophenyl]acetyl)-3-thiosemicarbazide, m.p. 203°–205° C.,
5. 1-(5-[p-methoxyphenyl]pentanoyl)-3-thiosemicarbazide, m.p. 112°–115° C.,
6. 1-(2-[5-chlorophenyl]acetyl)-3-thiosemicarbazide, m.p. 185°–187° C.,
7. 1-(2-[2,6-dichlorophenyl]acetyl)-3-thiosemicarbazide, m.p. 291°–293° C.,
8. 1-(2-[3,4-dichlorophenyl]acetyl)-3-thiosemicarbazide, m.p. 194°–196° C.,
9. 1-(2-[2,4-dichlorophenyl]acetyl)-3-thiosemicarbazide, m.p. 225°–226° C.,
10. 1-(2-[2-fluorophenyl]acetyl)-3-thiosemicarbazide, m.p. 150°–153° C.,
11. 1-(2-[3-fluorophenyl]acetyl)-3-thiosemicarbazide, m.p. 174°–177° C.,
12. 1-(2-[4-fluorophenyl]acetyl)-3-thiosemicarbazide, m.p. 162°–165° C.,
13. 1-(2-[2,3,6-trichlorophenyl]acetyl)-3-thiosemicarbazide, m.p. 227°–229° C.,
14. 1-(5-[p-chlorophenyl]pentanoyl)-3-thiosemicarbazide, m.p. 108°–111° C.,
15. 1-(7-phenylanoyl)-3-thiosemicarbazide, 101°–102° C.,
16. 1-(8phenyloctanoyl)-3-thiosemicarbazide, m.p. 92°–95° C., or
17. 1-(9-phenylnonanoyl)-3-thiosemicarbazide, m.p. 105°–107° C., respectively.

Step B

Following the procedure of Example 1, Step B, and starting with the appropriate intermediate of Step A of this Example, the following products are obtained:

1. 2-amino-5-(3-[phenylpropyl])-thiadiazole, m.p. 183°–185° C.,
2. 2-amino-5-(5-[phenylpentyl])-thiadiazole, m.p. 150°–151° C.,
3. 2-amino-5-(p-chlorobenzyl)-thiadiazole, m.p. 198°–199° C.,
4. 2-amino-5-(2-chlorobenzyl)-thiadiazole, m.p. 212°–213° C.,
5. 2-amino-5-(4-[p-methoxyphenylbutyl])-thiadiazole, m.p. 171°–173° C.,
6. 2-amino-5-(3-chlorobenzyl)-thiadiazole, m.p. 191°–193° C.,
7. 2-amino-5-(2,6-dichlorobenzyl)-thiadiazole, m.p. 213°–215° C.,
8. 2-amino-5-(3,4-dichlorobenzyl)-thiadiazole, m.p. 185°–186° C.,
9. 2-amino-5-(2,4-dichlorobenzyl)-thiadiazole, m.p. 210°–211° C.,
10. 2-amino-5-(2-fluorobenzyl)-thiadiazole, m.p. 197°–198° C.,
11. 2-amino-5-(3-fluorobenzyl)-thiadiazole, m.p. 186°–187° C.,
12. 2-amino-5-(4-fluorobenzyl)-thiadiazole, m.p. 210°–212° C.,
13. 2-amino-5-(2,3,6-trichlorobenzyl)-thiadiazole, m.p. 219°–221° C.,
14. 2-amino-5-(4-[p-chlorophenyl]butyl)-thiadiazole, m.p. 174°–176° C.,
15. 2-amino-5-(6-phenylhexyl)-thiadiazole, m.p. 162°–164° C.,
16. 2-amino-5-(7-phenylheptyl)-thiadiazole, m.p. 148°–150° C., or
17. 2-amino-5-(8-phenyloctyl)-thiadiazole, m.p. 149°–150° C., respectively.

EXAMPLE 3

Step A

Following the procedure of Example 1, Step A, and in place of 5-phenylvaleroylchloride and starting with 1. 6-(2,6-dimethylphenyl)-hexanoylchloride, or
2. 7-(2,6-dichlorophenyl)-heptanoylchloride, the following intermediates are obtained:

1. 1-(6-[2,6-dimethylphenyl]hexanoyl)-3-thiosemicarbazide, or
2. 1-(7-[2,6-dichlorophenyl]heptanoyl)-3-thiosemicarbazide.

Step B
Following the procedure of Example 1, Step B, and starting with the appropriate intermediate of Step A of this Example, the following products are obtained:

1. 2-amino-5-(5-[2,6-xylylpentyl])-thiadiazole, or
2. 2-amino-5-(6-[2,6-dichlorophenylhexyl])-thiadiazole.

EXAMPLE 4

Step A
Following the procedure of Example 1, Step A, and in place of 5-phenylvaleroylchloride and starting with 1. 2-phenylpropanoylchloride,
2. 3-phenylbutanoylchloride,
3. 4-phenylpentanoylchloride,
4. 5-(2,6-dimethylphenyl)hexanoylchloride,
5. 6-(2,6-dichlorophenyl)hyanoylchloride,
6. 7-(p-methoxyphenyl)octanoylchloride,
7. 8-phenylnonanoylchloride, or
8. 9-phenylundecanoylchloride, the following intermediates are obtained:

1. 1-(2-phenylpropnaoyl)-3-thiosemicarbazide,
2. 1-(3-phenylbutanoyl)-3-thiosemicarbazide,
3. 1-(4-phenylpentanoyl)-3-thiosemicarbazide,
4. 1-(5-[2,6-dimethylphenyl]hexanoyl)-3-thiosemicarbazide,
5. 1-(6-[2,6-dichlorophenyl]heptanoyl)-3-thiosemicarbazide,
6. 1-(7-[p-methoxyphenyl]octanoyl)-3-thiosemicarbazide,
7. 1-(8-phenylnonanoyl)-3-thiosemicarbazide, or
8. 1-(9-phenylundecanoylchloride, respectively.

Step B
Following the procedure of Example 1, Step B, and starting with the appropriate intermediate of Step A of this Example, the following products are obtained:

1. 2-amino-5-(1-phenethyl)-thiadiazole,
2. 2-amino-5-(2-methyl-2-phenethyl)-thiadiazole,
3. 2-amino-5-(3-methyl-3-phenylpropyl)-thiadiazole,
4. 2-amino-5-(4-methyl-4-[2,6-dimethylphenyl]butyl)-thiadiazole,
5. 2-amino-5-(5-methyl-5-[2,6-dichlorophenyl]pentyl)-thiadiazole,
6. 2-amino-5-(6-methyl-6-[p-methoxyphenyl]hexyl)-thiadiazole,
7. 2-amino-5-(7-methyl-7-phenylheptyl)-thiadiazole, or
8. 2-amino-5-(8-ethyl-8-phenyloctyl)-thiadiazole, respectively.

EXAMPLE 5

Step A
Following the procedure of Example 1, Step A, and in place of 5-phenylvaleroylchloride and starting with
1. 2-methyl-3-phenylpropanoylchloride,
2. 2-methyl-4-phenylbutanoylchloride,
3. 2-methyl-5-(2,6-dimethylphenyl)pentanylchloride,
4. 2-methyl-6-(2,6-dichlorophenyl)hexanoylchloride,
5. 2-methyl-7-(p-methoxyphenyl)heptanoylchloride,
6. 2-methyl-8-phenyloctanoylchloride, or
7. 2-methyl-9-phenylnonanoylchloride, the following intermediates are obtained:

1. 1-(2-methyl-3-phenylpropanoyl)-3-thiosemicarbazide,
2. 1-(2-methyl-4-phenylbutanoyl)-3-thiosemicarbazide,
3. 1-(2-methyl-5-[2,6-dimethylphenyl]pentanoyl)-3-thiosemicarbazide,
4. 1-(2-methyl-6-[2,6-dichlorophenyl]hexanoyl)-3-thiosemicarbazide,
5. 1-(2-methyl-7-[p-methoxyphenyl]heptanoyl)-3-thiosemicarbazide,
6. 1-(2-methyl-8-phenyloctanoyl)-3-thiosemicarbazide, or
7. 1-(2-methyl-9-phenylnonanoyl)-3-thiosemicarbazide, respectively.

Step B
Following the procedure of Example 1, Step B, and starting with the appropriate intermediate of Step A of this Example, the following products are obtained:

1. 2-amino-5-(1-methyl-1-phenethyl)-thiadiazole,
2. 2-amino-5-(1-methyl-1-phenylpropyl)-thiadiazole,
3. 2-amino-5-(1-methyl-1-[2,6-dimethylphenyl]butyl)-thiadiazole,
4. 2-amino-5-(1-methyl-1-[2,6-dichlorophenyl]pentyl)-thiadiazole,
5. 2-amino-5-(1-methyl-1-[p-methoxyphenyl]hexyl)-thiadiazole,
6. 2-amino-5-(1-methyl-1-phenylheptyl)-thiadiazole, or
7. 2-amino-5-(1-ethyl-1-phenyloctyl)-thiadiazole, respectively.

EXAMPLE 6

2-amino-5-(4-[phenylbutyl])-thiadiazole

A mixture of 17.7 g. of 5-phenylvaleroylchloride, 8.2 g. of thiosemicarbazide and 8.1 g. of phosphorous tribromide was heated to 60° C. when an exothermic reaction occurred raising the temperature to 100° C. The reaction mixture was cooled to 50° to 60° C. for 20 hours (when the evolution of hydrogen bromide ceased) and 100 cc. of ice water added. The mixture was then treated with 10 cc. of 50% sodium hydroxide solution, the resulting solid was washed with 2N sodium hydroxide solution and water, and the product crystallized from dimethylformamide and water, 2-amino-5-(4-[phenylbutyl])-thiadiazole, m.p. 172°–173° C.

EXAMPLE 7

Following the procedure of Example 6 and in place of 5-phenylvaleroylchloride and starting with 1. 4-phenylbutanoylchloride,
2. 6-phenylhexanoylchloride,
3. 2-(p-chlorophenyl)acetylchloride,
4. 2-(6-chlorophenyl)acetylchloride,
5. 5-(p-methoxyphenyl)pentanoylchloride,
6. 2-(5-chlorophenyl)acetylchloride,
7. 2-(2,6-dichlorophenyl)acetylchloride,
8. 2-(3,4-dichlorophenyl)acetylchloride,
9. 2-(2,4-dichlorophenyl)acetylchloride,
10. 2-(2-fluorophenyl)acetylchloride,
11. 2-(3-fluorophenyl)acetylchloride,
12. 2-(4-fluorophenyl)acetylchloride, 13. 2-(2,3,6-trichlorophenyl)acetylchloride,
14. 5-(p-chlorophenyl)pentanoylchloride,
15. 7-(phenylhepanoylchloride,
16. 8-phenyloctanoylchloride, or
17. 9-phenylnonanoylchloride, the following products are obtained:

1. 2-amino-5-(3-[phenylpropyl])-thiadiazole, m.p. 183°–185° C.,
2. 2-amino-5-(5-[phenylpentyl])-thiadiazole, m.p. 150°–151° C.,
3. 2-amino-5-(p-chlorobenzyl)-thiadiazole, m.p. 198°–199° C.,
4. 2-amino-5-(2-chlorobenzyl)-thiadiazole, m.p. 212°–213° C.,
5. 2-amino-5-(4-[p-methoxyphenylbutyl])-thiadizole, m.p. 171°–173° C.,
6. 2-amino-5-(3-chlorobenzyl)-thiadiazole, m.p. 191°–193° C.,
7. 2-amino-5-(2,6-dichlorobenzyl)-thiadiazole, m.p. 213°–215° C.,
8. 2-amino-5-(3,4-dichlorobenzyl)-thiadiazole, m.p. 185°–186° C.,
9. 2-amino-5-(2,4-dichlorobenzyl)-thiadiazole, m.p. 210°–211° C.,
10. 2-amino-5-(2-fluorobenzyl)-thiadiazole, m.p. 197°–198° C.,
11. 2-amino-5-(3-fluorobenzyl)-thiadiazole, m.p. 186°–187° C.,
12. 2-amino-5-(4-fluorobenzyl)-thiadiazole, m.p. 210°–212° C.,
13. 2-amino-5-(2,3,6-trichlorobenzyl)-thiadiazole, m.p. 219°–221° C.,
14. 2-amino-5-(4-[p-chlorophenyl]butyl)-thiadiazole, m.p. 174°–176° C.,
15. 2-amino-5-(6-phenylhexyl)-thiadiazole, m.p. 162°–164° C.,
16. 2-amino-5-(7-phenylheptyl)-thiadiazole, m.p. 148°–150° C., or
17. 2-amino-5-(8-phenyloctyl)-thiadiazole, m.p. 149°–150° C., respectively.

EXAMPLE 8

Following the procedure of Example 6, and in place of 5-phenylvaleroylchloride and starting with 1. 6-(2,6-dimethylphenyl)-hexanoylchloride, or
2. 7-(2,6-dichlorophenyl)-heptanoylchloride, the following products are obtained:

1. 2-amino-5-(5-[2,6-xylylpentyl])-thiadiazole, or
2. 2-amino-5-(6-[2,6-dichlorophenylhexyl])-thiadiazole.

EXAMPLE 9

Following the procedure of Example 6 and in place of 5-phenylvaleroylchloride and starting with 1. 2-phenylpropanoylchloride,
2. 3-phenylbutanoylchloride,
3. 4-phenylpentanoylchloride,
4. 5-(2,6-dimethylphenyl)hexanoylchloride,
5. 6-(2,6-dichlorophenyl)hyanoylchloride,
6. 7-(p-methoxyphenyl)octanoylchloride,
7. 8-phenylnonanoylchloride, or
8. 9-phenylundecanoylchloride, respectively, the following products are obtained:

1. 2-amino-5-(α-methylbenzyl)-thiadiazole,
2. 2-amino-5-(β-methylphenethyl)-thiadiazole,
3. 2-amino-5-(3-methyl-3-phenylpropyl)-thiadiazole,
4. 2-amino-5-(4-methyl-4-[2,6-dimethylphenyl]butyl)-thiadiazole,
5. 2-amino-5-(5-methyl-5-[2,6-dichlorophenyl]pentyl)-thiadiazole,
6. 2-amino-5-(6-methyl-6-[p-methoxyphenyl]hexyl)-thiadiazole,
7. 2-amino-5-(7-methyl-7-phenylheptyl)-thiadiazole, or
8. 2-amino-5-(8-ethyl-8-phenyloctyl)-thiadiazole, respectively.

EXAMPLE 10

Step A

Following the procedure of Example 4 and in place of 5-phenylvaleroylchloride and starting with 1. 2-methyl-3-phenylpropanoylchloride,
2. 2-methyl-4-phenylbutanoylchloride,
3. 2-methyl-5-(2,6-dimethylphenyl)pentanoylchloride,
4. 2-methyl-6-(2,6-dichlorophenyl)hexanoylchloride,
5. 2-methyl-7-(p-methoxyphenyl)heptanoylchloride,
6. 2-methyl-8-phenyloctanoylchloride, or
7. 2-methyl-9-phenylnonanoylchloride, respectively, the following products are obtained:

1. 2-amino-5-(α-methylphenethyl)-thiadiazole,
2. 2-amino-5-(1-methyl-3-phenylpropyl)-thiadiazole,
3. 2-amino-5-(1-methyl-4-[2,6-dimethylphenyl]butyl)-thiadiazole,
4. 2-amino-5-(1-methyl-5-[2,6-dichlorophenyl]pentyl)-thiadiazole,
5. 2-amino-5-(1-methyl-6-[p-methoxyphenyl]hexyl)-thiadiazole,
6. 2-amino-5-(1-methyl-7-phenylheptyl)-thiadiazole, or
7. 2-amino-5-(1-ethyl-8-phenyloctyl)-thiadiazole, respectively.

EXAMPLES 11 AND 12

Tablets and Capsules Suitable for Oral Administration

Tablets and capsules containing the ingredients indicated below may be prepared by conventional techniques and are useful as minor tranquilizers-sedative hypnotics at a dose of one tablet or capsule 2 to 4 times a day.

| Ingredients | Weight (mg.) tablet | capsule |
|---|---|---|
| 2-amino-5-(4-[phenylbutyl])-thiadiazole | 25 | 25 |
| tragacanth | 10 | — |
| lactose | 222.5 | 275 |
| corn starch | 25 | |
| talcum | 15 | |
| magnesium stearate | 2.5 | |

EXAMPLES 13 AND 14

Sterile Suspension for Injection and Oral Liquid Suspension

The following pharmaceutical compositions are formulated with the indicated amount of active agent using conventional techniques. The injectable suspension and the oral liquid suspension represent formulations useful as unit doses and may be administered as minor tranquilizers-sedative hypnotics. The injectable suspension is suitable for administration once a day whereas the oral liquid suspension is suitably administered 2 to 4 times per day for this purpose.

| Ingredients | Weight (mg.) Sterile Injectable Suspension | Oral Liquid Suspension |
| --- | --- | --- |
| 2-amino-5-(4-[phenyl-butyl])-thiadiazole | 25 | 25 |
| sodium carboxy methyl cellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g., Tween 80), U.S.P. | — | 5 |
| sorbitol solution, 70% U.S.P. | — | 2,500 |
| buffer agent to adjust pH for desired stability | q.s. | q.s. |
| water | for injection, q.s. to 1 ml. | q.s. to 5 ml. |

EXAMPLES 15 AND 16

Following the procedures of Examples 11 and 12, and in place of 2-amino-5-(4-[phenylbutyl])-thiadiazole starting with a final product of Examples 2, 3, 4, or 5, tablets and capsules may be prepared which are useful as minor tranquilizers-sedative hypnotics at a dose of one tablet or capsule 2 to 4 times a day.

EXAMPLES 17 and 18

Following the procedures of Examples 13 and 14, and in place of 2-amino-5-(4-[phenylbutyl])-thiadiazole starting with a final product of Examples 2, 3, 4, or 5, injectable suspensions and oral liquid suspensions may be prepared which are useful as minor tranquilizers-sedative hypnotics at a dose of one tablet or capsule 2 to 4 times a day.

What is claimed is:
1. The compound which is 2-amino-5-(4-[phenylbutyl])-thiadiazole.
2. The compound which is 2-amino-5-(3-[phenylpropyl])-thiadiazole.
3. The compound which is 2-amino-5-(5-[phenylpentyl])-thiadiazole.
4. The compound which is 2-amino-5-(p-chlorobenzyl)-thiadiazole.
5. The compound which is 2-amino-5-(2-chlorobenzyl)-thiadiazole.
6. The compound which is 2-amino-5-(4-[p-methoxyphenylbutyl])-thiadiazole.
7. The compound which is 2-amino-5-(3-chlorobenzyl)-thiadiazole.
8. The compound which is 2-amino-5-(2,6-dichlorobenzyl)-thiadiazole.
9. The compound which is 2-amino-5-(3,4-dichlorobenzyl)-thiadiazole.
10. The compound which is 2-amino-5-(2,4-dichlorobenzyl)-thiadiazole.
11. The compound which is 2-amino-5-(2-fluorobenzyl)-thiadiazole.
12. The compound which is 2-amino-5-(3-fluorobenzyl)-thiadiazole.
13. The compound which is 2-amino-5-(4-fluorobenzyl)-thiadiazole.
14. The compound which is 2-amino-5-(2,3,6-trichlorobenzyl)-thiadiazole.
15. The compound which is 2-amino-5-(4-[p-chlorophenyl]butyl)-thiadiazole.
16. The compound which is 2-amino-5-(6-phenylhexyl)-thiadiazole.
17. the compound which is 2-amino-5-(7-phenylheptyl)-thiadiazole.
18. The compound which is 2-amino-5-(8-phenyloctyl)-thiadiazole.

\* \* \* \* \*